US00PP11612P

United States Patent [19]

Strickland

[11] Patent Number: Plant 11,612

[45] Date of Patent: Oct. 31, 2000

[54] SOUTHERN MAGNOLIA TREE NAMED 'TMGH'

[75] Inventor: Thomas Julian Strickland, Statesboro, Ga.

[73] Assignee: Tree Introductions, Inc., Bishop, Ga.

[21] Appl. No.: 09/158,599

[22] Filed: Sep. 22, 1998

[51] Int. Cl.[7] ..... A01H 5/00

[52] U.S. Cl. ..... Plt./223

[58] Field of Search ..... Plt./223

[56] References Cited

U.S. PATENT DOCUMENTS

P.P. 2,617 4/1966 Van Rensselaer ..... Plt./223

*Primary Examiner*—Howard J. Locker
*Assistant Examiner*—Wendy A. Baker
*Attorney, Agent, or Firm*—Klarquist Sparkman Campbell Leigh & Whinton LLP

[57] ABSTRACT

A Southern Magnolia named 'TMGH' having an upright compact growth habit with a dense foliage canopy, a dominant leader with secondary branches ascending upwardly, lustrous dark green, narrow leaves with a rusty-brown back, a dense, fibrous root system, and also capable of being reproduced reliably from vegetative cuttings.

4 Drawing Sheets

DESCRIPTION

The present invention relates to a new and distinct variety of *Magnolia grandiflora,* Southern Magnolia, which has been given the varietal name 'TMGH'.

I discovered my new variety in 1993 as a chance seedling of 'Hasse' Southern Magnolia (believed unpatented) growing in a production field at a nursery in Bulloch County, Ga. This new variety originated as a seedling planted in spring 1989, and was then transplanted into the field in Jul. 1989 as a six to eight inch liner. It is now nine years old. As I observed the original tree of my new variety since 1993, the uniqueness of this tree became apparent because of its compact, narrow, dark green leaves with rusty-brown undersides and dense, narrow, upright growing habit. This new tree resembles 'Hasse' by virtue of its narrow columnar growing habit and leaf shape and color. However, it is much denser than 'Hasse' and has a much more fibrous root system. In 1993, this original tree of my new variety tree was successfully propagated by softwood cuttings. In 1995, it was determined that this tree had a superior root system compared to 'Hasse'.

I have observed this tree of my new variety for since 1993 and believe it is particularly useful in landscape setting where upright, tight evergreen tree forms are important, such as along buildings or in parking lots or in any situation where fast-growing, consistent screens are needed as windbreaks or as control for noise pollution, especially in urban areas where space is at a premium. The superior root system is expected to result in more successful transplanting than with some other Magnolias.

These unique qualities of my new variety, namely a narrow, upright, dense habit and dark green leaves with rusty-brown backing along with a fibrous root system, offer a combination not represented by any other cultivar or seedling known to me.

Southern Magnolia is a large evergreen tree that matures between sixty to eighty feet high and thirty to fifty feet wide, is somewhat adaptable to soil and climate, and has a native range from North Carolina to Florida and Texas. Southern Magnolia is a popular tree throughout its range, and there is a need for a dense, narrow, compact upright form that will lend itself to growing situations where space is limited. Consequently, a new variety of Southern Magnolia which has a dense, narrow, upright habit and lustrous dark green foliage and which displays clonal consistency is particularly useful.

My new variety has been asexually propagated from softwood cuttings at my direction in Bulloch County, Ga.

This propagation and observation of the resulting progeny in Bulloch County, Ga. have proven the characteristics of my new variety to be firmly fixed. Furthermore, these observations have confirmed that my new variety represents a new and improved variety of Southern Magnolia as particularly evidenced by the unique dense, narrow, upright growth habit and which can reliably be asexually propagated using vegetative propagation techniques.

The accompanying photographs depict the color of the tree and foliage of my new variety as nearly true as is reasonably possible to make the same in a color illustration of this character.

My 'TMGH' variety of Southern Magnolia has not been observed under all growing conditions and thus variations may occur as a result of different growing conditions. The following is a detailed description of my new variety of Southern Magnolia with color terminology in accordance with The Royal Horticultural Society Colour Chart (R.H.S.) published by The Royal Horticultural Society of London. The observations are of the original tree of my new variety growing at 1900 Cole Springs Road, Bishop, Ga.

Figure 1:
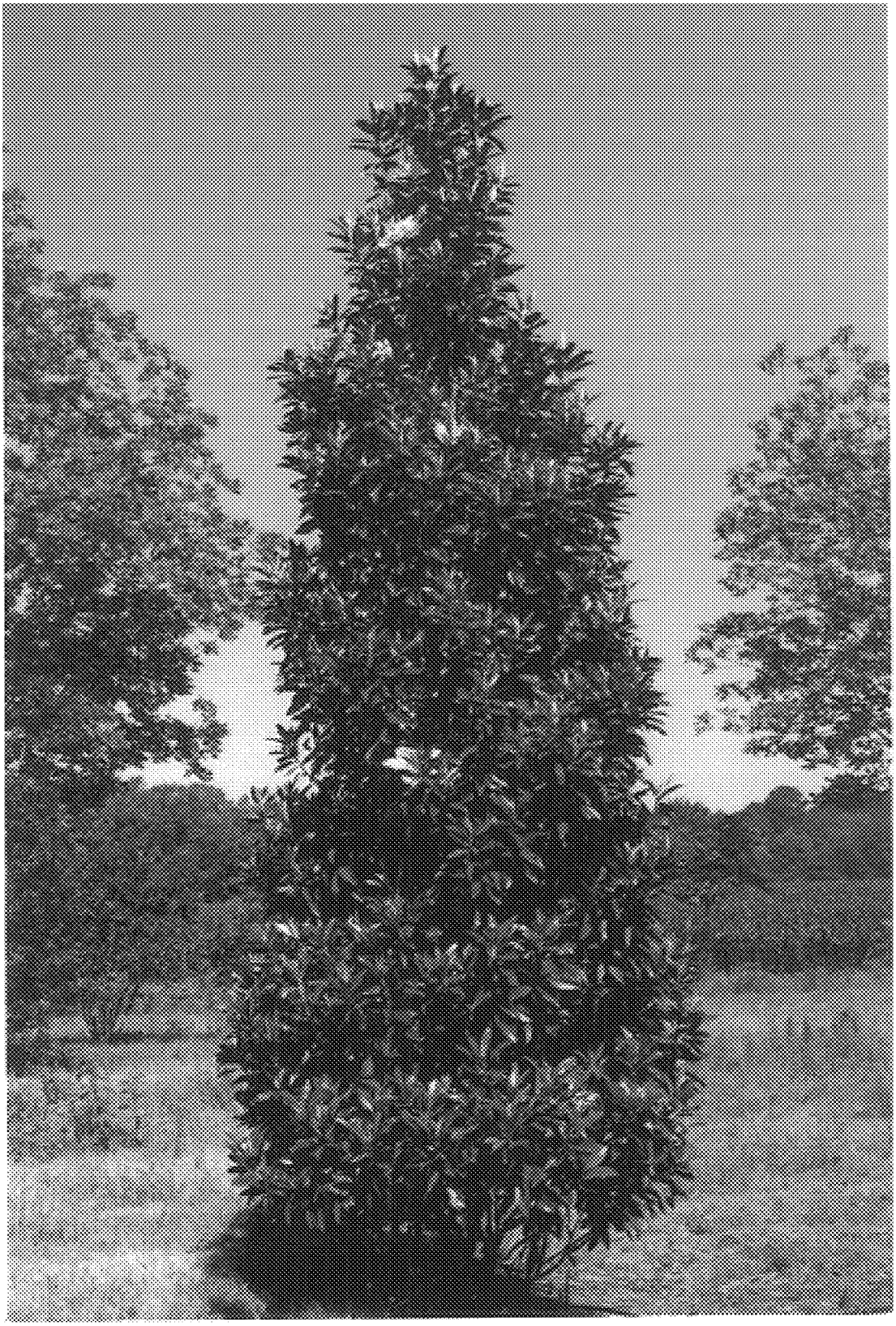
FIG. 1 is a photograph of an entire tree of my new variety.
Figure 2:
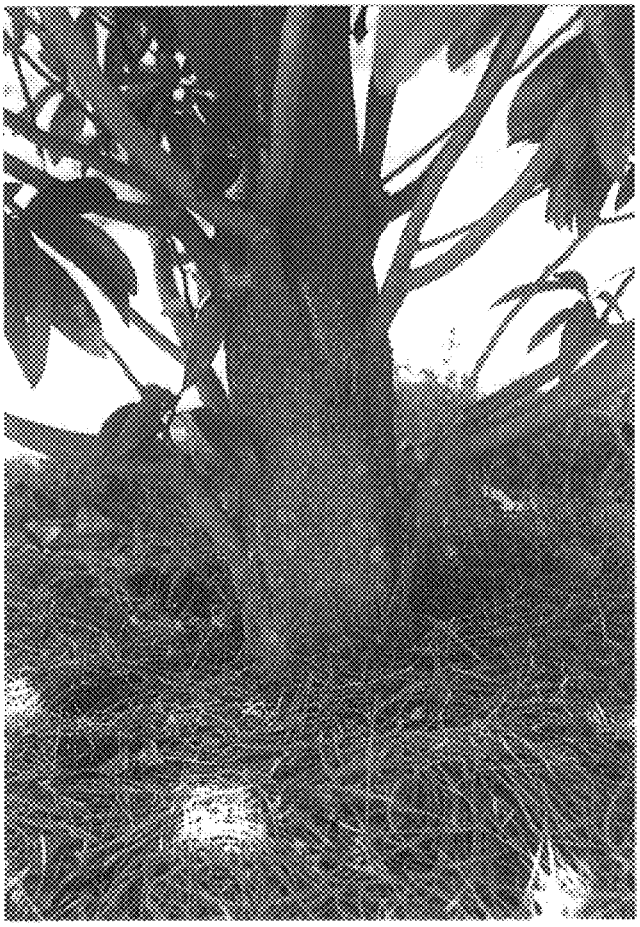
FIG. 2 is a close up of a trunk of my new variety showing mature bark.
Figure 3:
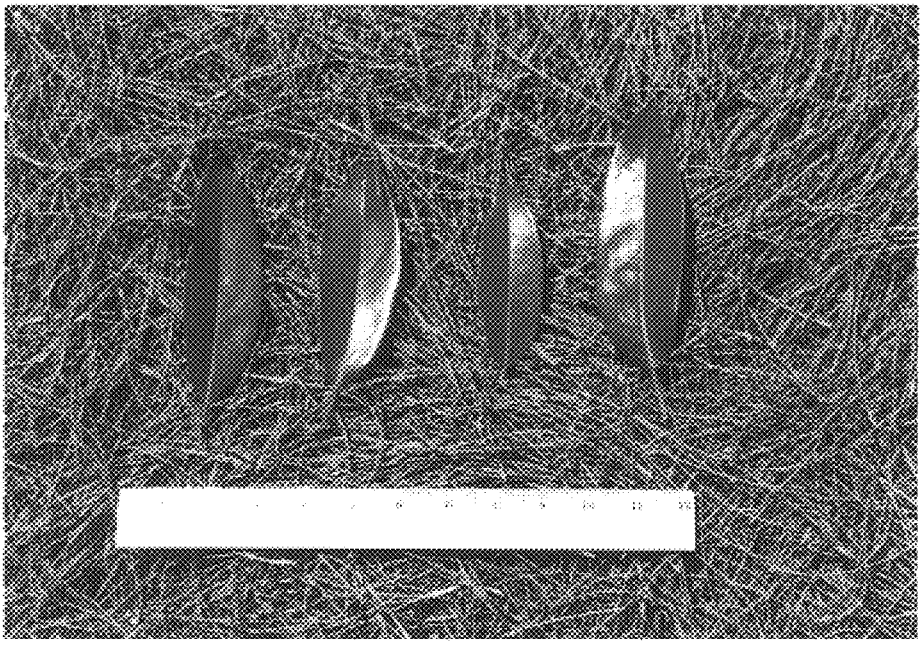
FIG. 3 is a close up of the upper surface of several leaves from a tree of my new variety.
Figure 4:
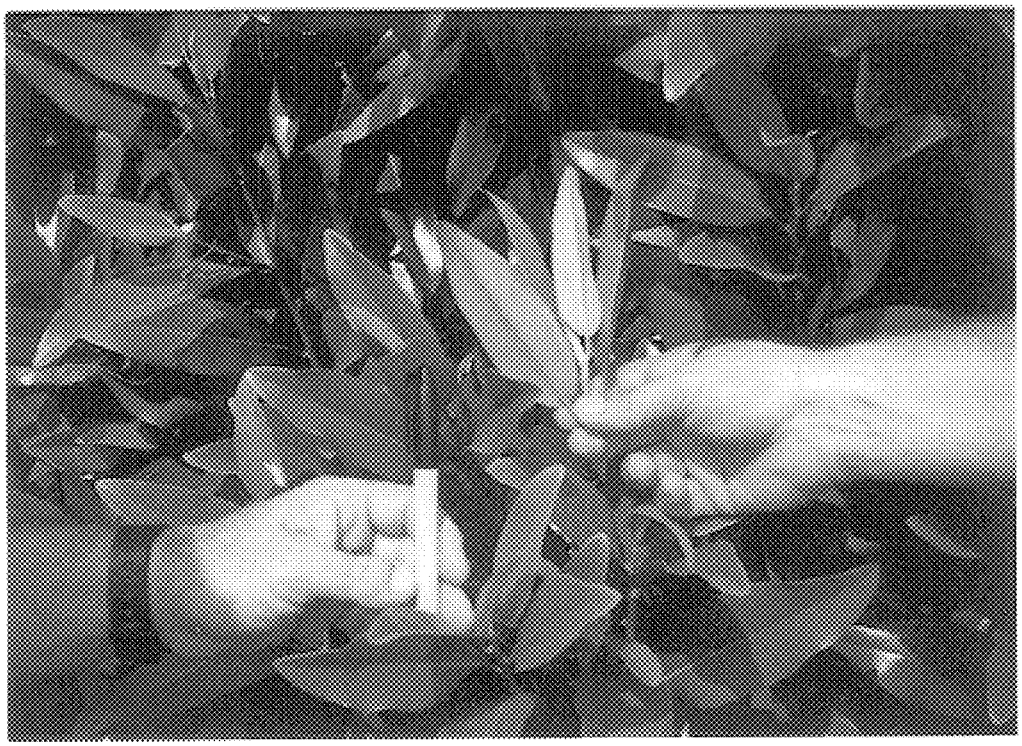
FIG. 4 is a close up of the lower surface of several leaves from a tree of my new variety.
Figure 5:
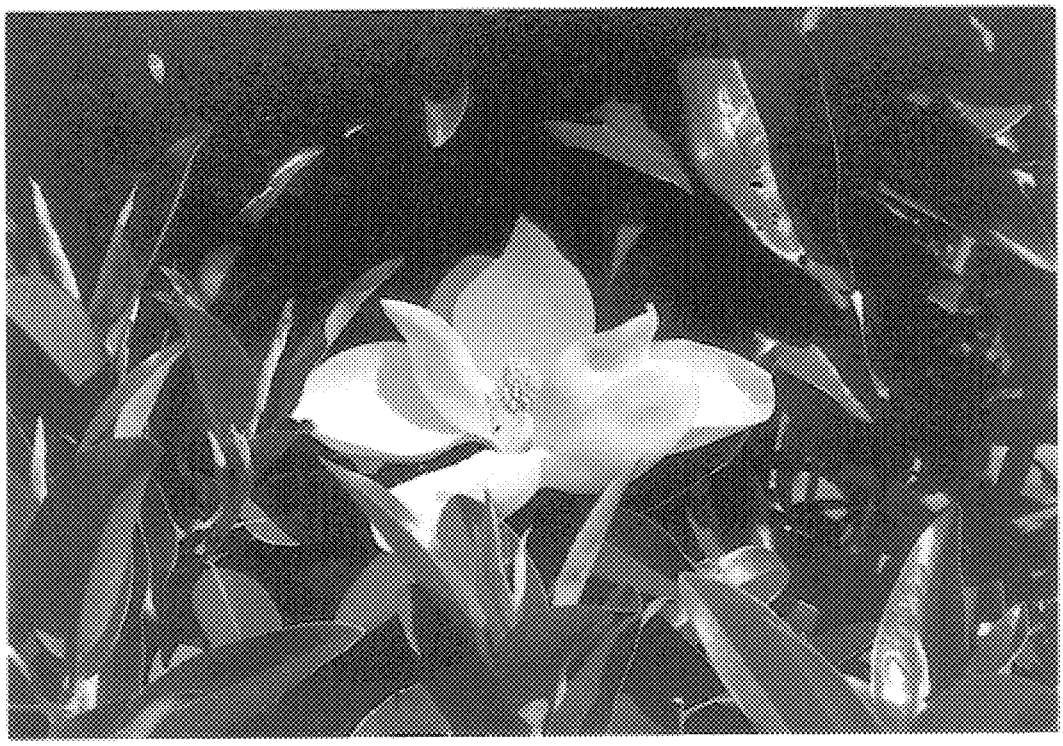
FIG. 5 is a close up of the flower from a tree of my new variety.
Figure 6:
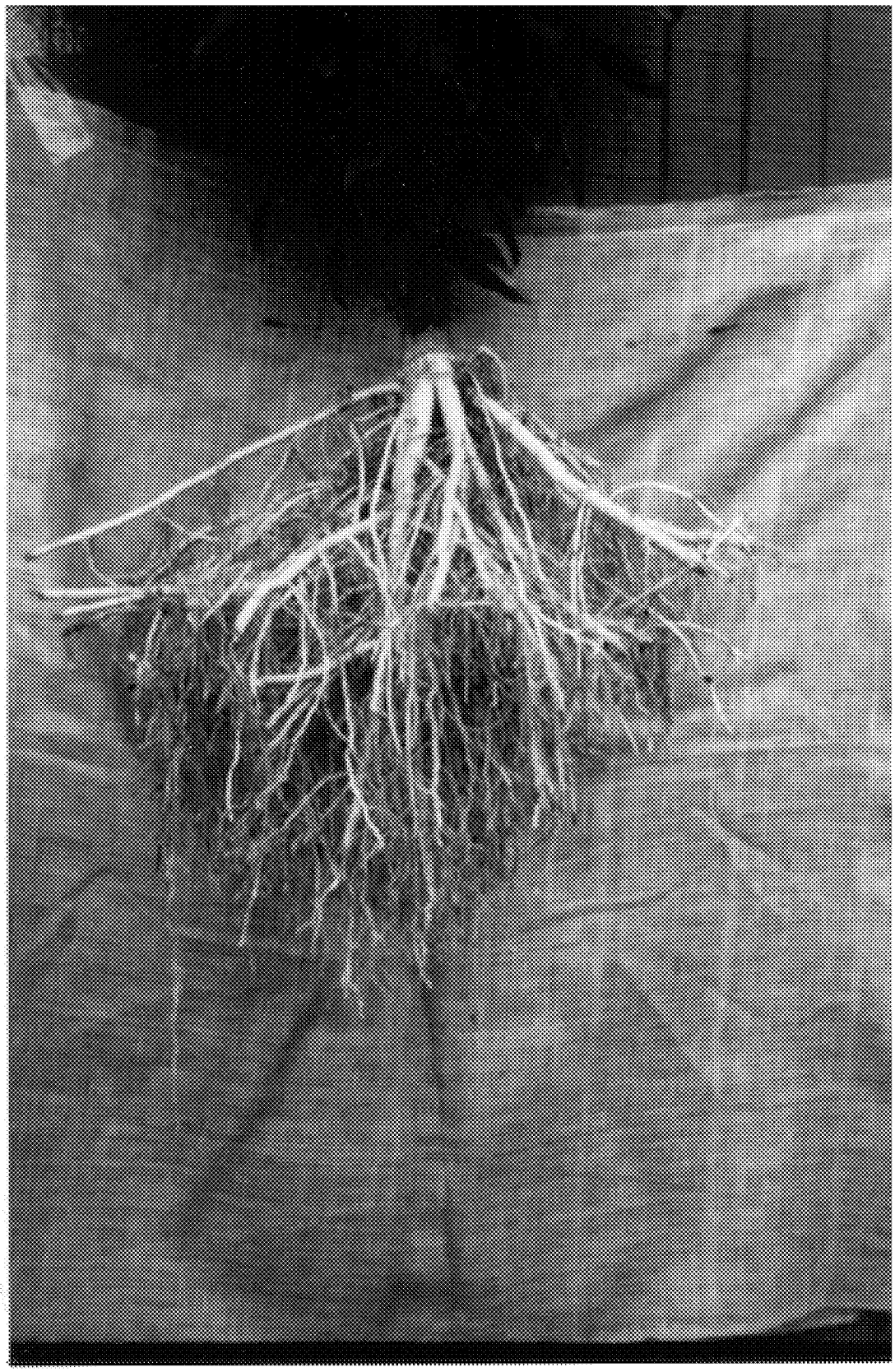
FIG. 6 is a photograph of the root system of my new variety.

My new variety of Southern Magnolia is characterized by dense upright habit (FIG. 1), narrow, lustrous dark green leaves with rusty-brown backing (FIGS. 3 and 4), and a dense, fibrous root system (FIG. 6). It is also a fast grower. The original tree has averaged at least two feet of growth per year. In 1989, the initially discovered tree of my new variety was planted as a seed and then transplanted from a one quart pot to a production field in Bulloch County, Ga. My new variety was first propagated from softwood cuttings in 1993.

In 1998, the original tree was eighteen feet high and eight feet wide with a height to width ratio of 2.25. This upright compact form with dense foliage and branching distinguishes my new variety from typical *Magnolia grandiflora* trees. Most Southern Magnolias are pyramidal.

My new tree maintains a tight branching pattern which contributes to its narrow-columnar habit. In contrast, most seedlings and cultivars which I have observed do not maintain this narrow habit. The Southern magnolia cultivars which do have a narrow habit are 'Hasse' and 'MGTIG' (U.S. Plant Pat. No. 9,243), but my new cultivar is demonstrably different from these two by virtue of its root system when compared to 'Hasse' and by virtue of its leaf when compared to 'MGTIG'. The unique growth habit of my new variety facilitates its use in areas where growing space is restricted, particularly along streets with buildings or sites which will not accommodate a broader canopy and as a screen or hedge where space is limited.

My new variety is distinctly different from 'Hasse' in that it is denser than 'Hasse' with a superior root system. 'Hasse' typically has a very coarse root system that limits successful transplanting. My new variety has a very dense and fibrous root system which facilitates transplanting (FIG. 6). My new variety is distinctly different from 'MGTIG' in that my new variety has a more lustrous dark green leaf which is smaller, flatter (FIG. 3), and not cupped like that of 'MGTIG'. Also, my new variety has a rusty brown backing to the leaf (FIG. 4) which is very different from 'MGTIG', which has a very green and glabrous backing. My new variety is also tighter with a higher height to width ratio compared to 'MGTIG'.

My new tree has a branching habit and dendritic pattern of single leader (bole). Secondary branches at the base of the tree emerge at sixty degree angles to the main trunk and sweep upward to thirty degree angles. Secondary branches at the top of the tree emerge at thirty degree angles to the main leader and sweep upward to ten degree angles. Branches are uniformly and densely borne around the central leader with no large gaps from one branch insertion to the next. As a result, as can be seen from FIG. 1, the tree of my new variety is uniformly branched and symmetrical with a dense canopy. In contrast, traditional seedling Southern Magnolias and most of the cultivars are usually more open and in youth must be pruned to produce an upright habit, and generally become more open with age.

The lower trunk and larger branches are typical of the species.

The summer leaves are typically darker than those of the species and most other cultivars, being lustrous dark green above and rusty-brown beneath. The upper leaf surface is lustrous dark green (R.H.S. 139A). The lower leaf surface is rusty brown (R.H.S. 165B). The leaf of the new variety typically has an extremely narrow edge margin which is yellow-green in color (R.H.S. 151A). the mature leaf averages six to eight inches long, one and one-half to two and one-half inches wide, ten to twelve vein pairs, with one-half to one and one-half inch long petioles. The leaf shape is lanceolate-elliptical, which is narrower than that of the species or of other cultivars. The undersides of the leaves are rusty-brown and pubescent, especially on new leaves, becoming grayer and less pubescent with age. Pubescence is typical of the species, but there are varying degrees and shades among the cultivars. Leaf arrangement is whorled and margins are entire, both typical of the species.

Flowers and fruits, insofar as observed as of this time, appear to be typical of the species, and the original tree of the new variety initiated flowers in the spring of 1997 when it was eight years old.

THE PLANT

Parentage:Chance Southern Magnolia seedling of 'Hasse' Southern Magnolia, growing in a cultivated area of a production nursery in Bulloch County, Ga.

Tree shape: Narrow-columnar.

Trunk: Dominant central leader, gray-brown (R.H.S. 198A) in color, typical of the species. Girth of fifty 4 year-old trees of my new variety growing in Oconee County, Ga., averaged about 1.7 inches when measured at a height of 6 inches above ground.

Bark: Gray brown (R.H.S. 198A). Typical of the species. Bark surface texture is rough.

Mature bark color: (Observed in the original tree of my new variety) Gray brown (R.H.S. 198A); typical of the species.

Branches: Ascending, emerging from the dominant leader at an angle of sixty degrees (base) and thirty degrees (top). Branch size is highly dependent on growing conditions. A sampling of a number of one year-old branches of trees growing in Oconee County, Ga., averaged 0.25 inches in diameter. One year old branches are dark green in color.

Leaves: Leaf shape is lanceolate-elliptical and narrower than the species. Both the leaf apex and leaf base have a slightly acute shape.

Leaf surface: Upper leaf surface is lustrous dark green (R.H.S. 139A) and glabrous. The lower surface is pubescent rusty-brown (R.H.S. 165B).

Leaf size: Leaves average six to eight inches long, one and one-half to two and one-half inches wide, ten to twelve vein pairs, with one to two inch long petioles.

Buds, flowers, and fruit: Observed in the original tree of my new variety to be like those of the species. Colors for flower parts (stamens, anthers, filaments, pollen, stigmas, petals) are typical for the species. Petals are a creamy white (R.H.S. 155C). Solitary flowers typically are 8–10 inches in diameter with 8 concave petals. Flower texture is thick, smooth, soft and leathery. Flowers have a sweet, strong fragrance. In terms of fertility, flowers are perfect. Fruit is not noticeably different from the species insofar as has been observed. Fruit matures approximately 6 months after beginning of flowering and is approximately 4 to 5 inches long. Fruit shape is an aggregate of follicles. The fruits are a rusty red-brown and the seeds are red.

Timing and duration of bloom: Based on observations in Bulloch County, Ga. in Spring of 1999, bud burst was observed to commence at about mid-April. Individual blooms at this location typically lasted about 10 days. The plant at this location was observed at this time to bloom for a period of about 60–70 days. The information on blooming is expected to vary with growing conditions and locale. In observations to date, plants of my new variety have been observed to begin blooming at about less than one year of age.

Root system: Dense and fibrous, more fibrous than the root system of 'Hasse', with a higher density and root to soil interface. Tree survivability and thrivability are enhanced, compared to 'Haase'. Time to rooting is faster than 'Haase'.

Disease resistance: No unusual susceptibility to disease has been observed.

I claim:

1. A new and distinct variety of Southern Magnolia tree substantially as herein shown and described, characterized particularly as to novelty by its unique narrow-columnar dense growth habit, narrow, lustrous dark green leaves with a rusty-brown back, and a dense, fibrous root system.

* * * * *